United States Patent
Lombardi

(10) Patent No.: US 7,998,114 B2
(45) Date of Patent: Aug. 16, 2011

(54) METHOD AND APPARATUS FOR REGULATING PRESSURE DURING MEDICAL PROCEDURES

(75) Inventor: Pierluca Lombardi, Miami Beach, FL (US)

(73) Assignee: MAQUET Cardiovascular LLC, San Jose, CA (US)

( * ) Notice: Subject to any disclaimer, the term of this patent is extended or adjusted under 35 U.S.C. 154(b) by 176 days.

(21) Appl. No.: 10/751,765

(22) Filed: Jan. 5, 2004

(65) Prior Publication Data
US 2004/0138615 A1 Jul. 15, 2004

(51) Int. Cl.
*A61M 1/00* (2006.01)

(52) U.S. Cl. ........................................... 604/118

(58) Field of Classification Search .................. 604/249, 604/118, 33, 123, 127, 129, 246–47; 417/385; 137/71, 115.28, 6, 115.26
See application file for complete search history.

(56) References Cited

U.S. PATENT DOCUMENTS

| | | | |
|---|---|---|---|
| 4,329,985 A | | 5/1982 | Bonchek et al. |
| 4,403,988 A | * | 9/1983 | Binard et al. ................. 604/118 |
| 4,501,291 A | * | 2/1985 | Siegrist ........................ 137/529 |
| 4,550,747 A | * | 11/1985 | Woodworth et al. ...... 137/487.5 |
| 4,623,335 A | * | 11/1986 | Jackson ....................... 604/118 |
| 5,064,193 A | * | 11/1991 | Sainte et al. .................. 482/113 |
| 5,250,034 A | * | 10/1993 | Appling et al. .......... 604/164.02 |
| 5,558,139 A | * | 9/1996 | Snyder ........................... 141/95 |
| 5,630,935 A | * | 5/1997 | Treu .............................. 210/130 |
| 5,657,499 A | * | 8/1997 | Vaughn et al. ..................... 5/654 |
| 5,685,851 A | * | 11/1997 | Murphy et al. ............... 604/150 |
| 5,743,257 A | * | 4/1998 | Koehler et al. .......... 128/205.24 |
| 5,928,182 A | * | 7/1999 | Kraus et al. ....................... 604/9 |
| 2003/0139702 A1 | * | 7/2003 | Renz et al. ...................... 604/74 |
| 2004/0230157 A1 | * | 11/2004 | Perry et al. ................. 604/99.02 |
| 2005/0038421 A1 | * | 2/2005 | Joye et al. ....................... 606/20 |

FOREIGN PATENT DOCUMENTS

| | | |
|---|---|---|
| EP | 0 032 826 A | 7/1981 |
| FR | 1 435 963 A | 6/1966 |

OTHER PUBLICATIONS

Supplementary European Search Report for EP 04 70 0200 dated Dec. 21, 2007.

* cited by examiner

*Primary Examiner* — Theodore J Stigell
*Assistant Examiner* — Andrew M Gilbert
(74) *Attorney, Agent, or Firm* — Alan W. Cannon; Law Office of Allen W. Cannon

(57) ABSTRACT

A method and apparatus are provided for regulating pressure applied during a medical procedure, including an inelastic housing enclosing an inner volume, a housing having a first and second end; an aperture in the housing, the aperture for coupling to an element for applying a pressure during a medical procedure, the element having an inner volume communicated with the inner volume of the housing; and a pressure-operated valve coupled to the housing for providing access to the inner volume of the housing when pressure in the housing is above a threshold, whereby the valve releases pressure from within the inner volume of the housing. The method and apparatus are particularly useful in preparation of conduits such as veins and arteries during grafting procedures.

15 Claims, 3 Drawing Sheets

METHOD AND APPARATUS FOR REGULATING PRESSURE DURING MEDICAL PROCEDURES

BACKGROUND OF THE INVENTION

1. Field of the Invention

This invention generally relates to medical procedures including the application of a pressure and, especially, to the field of vein grafting and preparation of a vein during vein grafting.

2. Description of Related Art

The first aortocoronary vein graft implantation in a human being was performed by Garrett and colleagues in May 1961. The subsequent pioneering work of Favaloro ushered in the era of surgical revascularization for the global epidemic of ischemic heart disease. Ironically, with the demonstration of the dramatic benefits obtainable by saphenous vein grafting came recognition of the ultimately palliative nature of the operation, due to the development of accelerated atherosclerosis within the saphenous vein conduits. During the first year after bypass surgery up to 15% of venous grafts occlude. In addition, between 1 and 6 years after bypass surgery the graft occlusion rate is 1% to 2% per year, and between 6 and 10 years the occlusion rate raise to 4% per year. By 10 years after surgery less than 60% of vein grafts are patent and only 50% of patent vein grafts are free of significant stenosis.

Reflecting this graft and native vessel patency rate, angina recurs in up to 20% of patients during the first year after bypass surgery using saphenous vein grafting and in 4% of patients annually during the ensuing 5 years. Further revascularization, either reoperative bypass surgery or percutaneous intervention, is required in 4% of patients by 5 years, 19% of patients by 10 years, and 31% of patients by 12 years after initial bypass surgery.

"Saphenous vein graft disease" is composed of three discrete processes: thrombosis, intimal hyperplasia, and atherosclerosis. These processes, although more or less temporally distinct, are interlinked pathophysiologically in the evolution of vein graft disease. Between 3% and 12% of saphenous vein grafts occlude, with or without symptoms, within the first month after bypass surgery. At this early stage, the principal underlying mechanism is graft thrombosis caused by a combination of alterations in the vessel wall, changes in blood rheology, and altered flow dynamics, as classically defined in Virchow's triad.

Even when performed under optimal conditions, the harvesting of venous conduits is associated with focal endothelial disruption. In particular, the high pressure distension used to overcome venospasm and to reveal reliably all unsecured side branches during harvesting causes prominent endothelial cell loss and medial damage. It was found that even the most skillful practitioner could not readily detect the relatively high pressures (600 to 700 mm Hg) generated by the syringe during harvesting, because a vein in spasm has a small diameter and allows wall tension (as defined by Laplace's Law).

Loss of the endothelial monolayer results in the accumulation of fibrin on the luminal surface, the adherence of platelets and neutrophils and a reduction in tissue plasminogen activator (tPA) production. Endothelial loss also activates the extrinsic coagulation cascade by tissue factor that is constitutively expressed in the exposed subendothelium. Tissue factor is also expressed, within 2 hours of initiating cardiopulmonary bypass, on the surfaces of endothelial cells activated by inflammatory cytokines.

In addition, saphenous veins, particularly when denuded, are highly sensitive to circulating vasoconstrictors, including the most potent endogenous vasoconstrictor, endothelin. The circulating concentration of endothelin-1 shows a marked initial rise, followed by an additional slower increment, after the onset of cardiopulmonary bypass and the resulting venoconstriction response may further attenuate flow and promote stasis.

Therefore a need exists to overcome the problems with the prior art as discussed above, and particularly for a way to more efficiently harvest saphenous veins so as to avoid increased pressure within the vein during the vein distention procedure.

SUMMARY OF THE INVENTION

A method and apparatus for preparing a vein for grafting is disclosed. In an embodiment of the present invention, the apparatus includes a first element for inserting liquid into a vein, the first element including an inelastic housing enclosing an inner volume. The apparatus further includes a second element for regulating pressure within the first and second elements, the second element including an inelastic housing enclosing an inner volume. The second element is coupled to the first element such that the inner volume of the second element is continuous with the inner volume of the first element. The apparatus further includes a pressure sensor or pressure-operated valve coupled to the second element for measuring pressure within the inner volume of the second element. The apparatus further includes a valve coupled to the second element and providing access to the inner volume of the second element. If the pressure sensor senses or is exposed to pressure above a threshold, the valve releases pressure from the inner volumes of the first and second elements.

In another embodiment of the present invention, the method for preparing a vein for grafting includes extracting a portion of a vein and connecting a first end of the vein that was extracted to a coupling. A seal is created between the coupling and the vein and the coupling provides access to an inner volume of the vein. The method further includes occluding the second end of the vein and inserting a liquid into the vein via the coupling using an apparatus. The apparatus includes a first element for inserting liquid into a vein, the first element including an inelastic housing enclosing an inner volume. The apparatus further includes a second element for regulating pressure within the first and second elements, the second element including an inelastic housing enclosing an inner volume. The second element is coupled to the first element such that the inner volume of the second element is continuous with the inner volume of the first element. The apparatus further includes a pressure sensor or pressure-operated valve coupled to the second element for measuring pressure within the inner volume of the second element a valve coupled to the second element and providing access to the inner volume of the second element. If the pressure sensor senses or is exposed to pressure above a threshold, the valve releases pressure from the inner volumes of the first and second elements.

In another embodiment of the present invention, an apparatus for regulating intravascular pressure during vein distention includes an inelastic housing enclosing an inner volume, the housing having a first and second end. The apparatus further includes an aperture on the first end of the housing, the aperture for coupling to an element having an inner volume such that the inner volume of the housing is continuous with the inner volume of the element. The apparatus further includes a pressure sensor or pressure-operated valve coupled to the housing for measuring pressure within the inner volume of the housing and a valve coupled to the housing and providing access to the inner volume of the housing. If the pressure sensor senses or is exposed to pressure above a threshold, the valve releases pressure from within the inner volume of the housing.

The aforementioned apparatus are not only aids in safe distention of vein grafts, but are also cost-effective, easy to use, and reliable. Further, the apparatus is well suited to safe application of pressure in other medical procedures as well.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings, wherein FIG. 1 schematically illustrates an apparatus in accordance with the present invention;

FIG. 3 shows an alternative embodiment of an apparatus in accordance with the present invention which provides for adjustable setting of the maximum pressure.

DETAILED DESCRIPTION

The invention relates to an apparatus for controlling the application of pressure during a medical procedure so as to reliably control or regulate the maximum pressure, or maximum negative pressure, which is applied during such a procedure.

As set forth above, one area where such an apparatus has excellent advantage in use is during preparation of a vein graft, since limiting the application of excessive pressure can provide a conduit such as a vein or artery which is significantly less damaged than such a conduit harvested using conventional processes that can expose the conduit to excessive pressure.

According to one embodiment, the present invention overcomes problems with the prior art by providing a vein graft preparation apparatus that controls pressure within a vein graft during the distention process.

In such a procedure, a portion of a conduit such as a vein or artery is extracted and connected to the apparatus of the present invention at one end. The other end is occluded, and fluid is inserted into the conduit to distend same. The apparatus of the present invention serves to regulate pressure applied to the conduit by the fluid.

Figure 1:
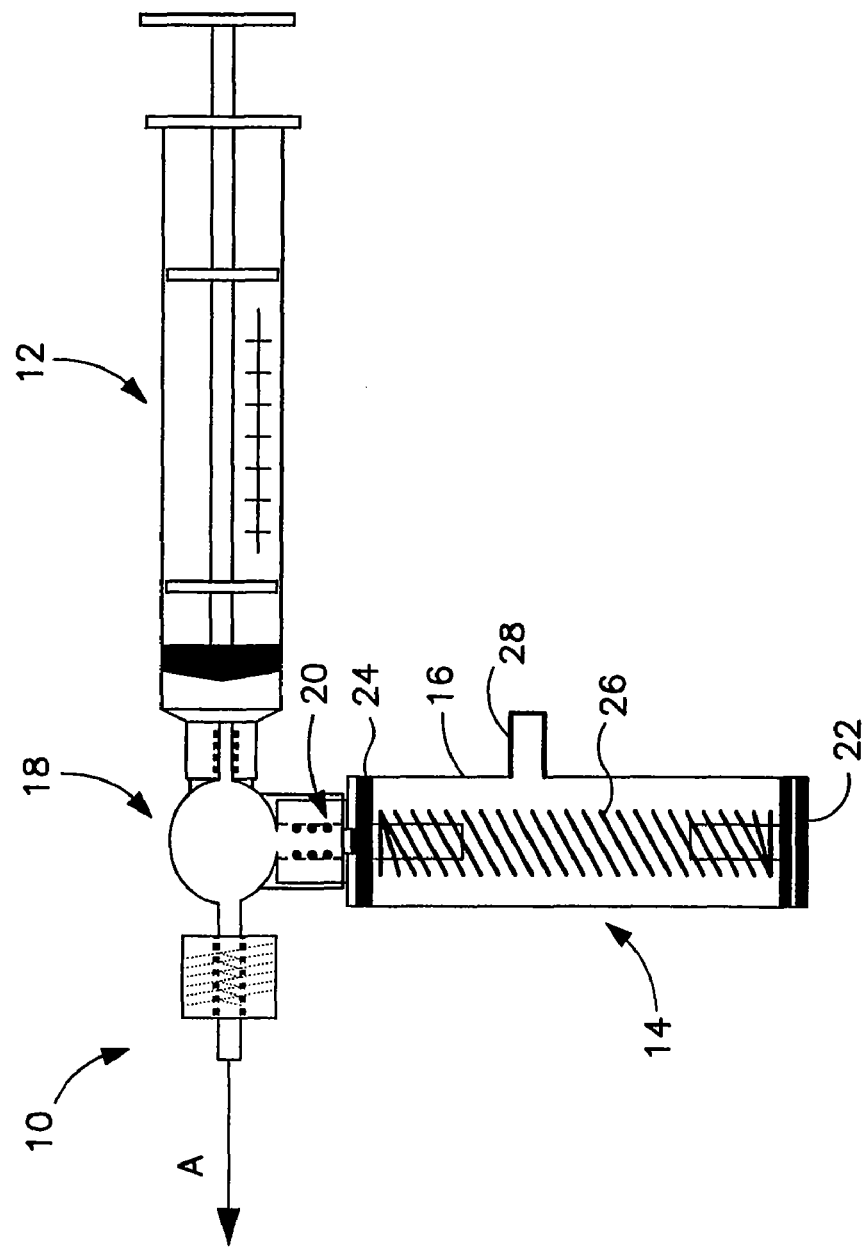

The present invention provides an apparatus that limits the hydrostatic pressure used in this case to distend a vein graft under a preset level. FIG. 1 illustrates a vein graft preparation apparatus 10 in one embodiment of the present invention. The apparatus 10 includes a first-element, in this case a standard syringe 12, for inserting fluid, preferably liquid, into the vein, and a second or pressure regulation element 14 used in conjunction with vein graft preparation apparatus 10. Pressure regulation element 14 includes a plastic cylinder 16 that attaches and locks into a three-way "stopcock" 18 with syringe 12. The pressure regulation element 14 preferably attaches substantially perpendicular to the syringe 12 that will be injecting fluid to the vein.

During the procedure, the conduit is monitored for leakage from side branches or the like. If such leakage is detected, the side branch can be occluded so as to improve the conduit for subsequent use.

Pressure regulation element 14 is open on one end 20 in order to attach to stopcock 18, and is closed on the opposite end 22. A pressure operated valve is advantageously coupled, either directly or in fluid communication with, element 14. This valve can be provided as follows. Within cylinder 16, there is a rubber stopper or piston 24 that sits on one end of a metal coil or spring 26. The rubber stopper is located nearer to open end 20 of the cylinder 16, in its resting position. On a lateral side of the cylinder, there is an orifice or opening 28 that can extend preferably substantially perpendicular from cylinder 16. Orifice 28 on cylinder 16 is located at the maximum allowed pressure level, or threshold pressure, that can be administered in the relevant medical procedure, in this case a safe maximum pressure to prevent damage to the vein. The purpose of orifice 28 is to ensure that excessive pressure is not applied when distending the vein. As fluid is injected into the vein, schematically illustrated by arrow A, the device will respond to and/or measure the pressure that is being applied. The fluid pressure will force rubber stopper 24 to contract coil 26 until fluid reaches orifice 28 of cylinder 16. At that point fluid and pressure will be relieved through orifice 28. As fluid is released through orifice 28, the pressure in the system will be equalized, preventing over-distending of the vein graft.

Figure 2:
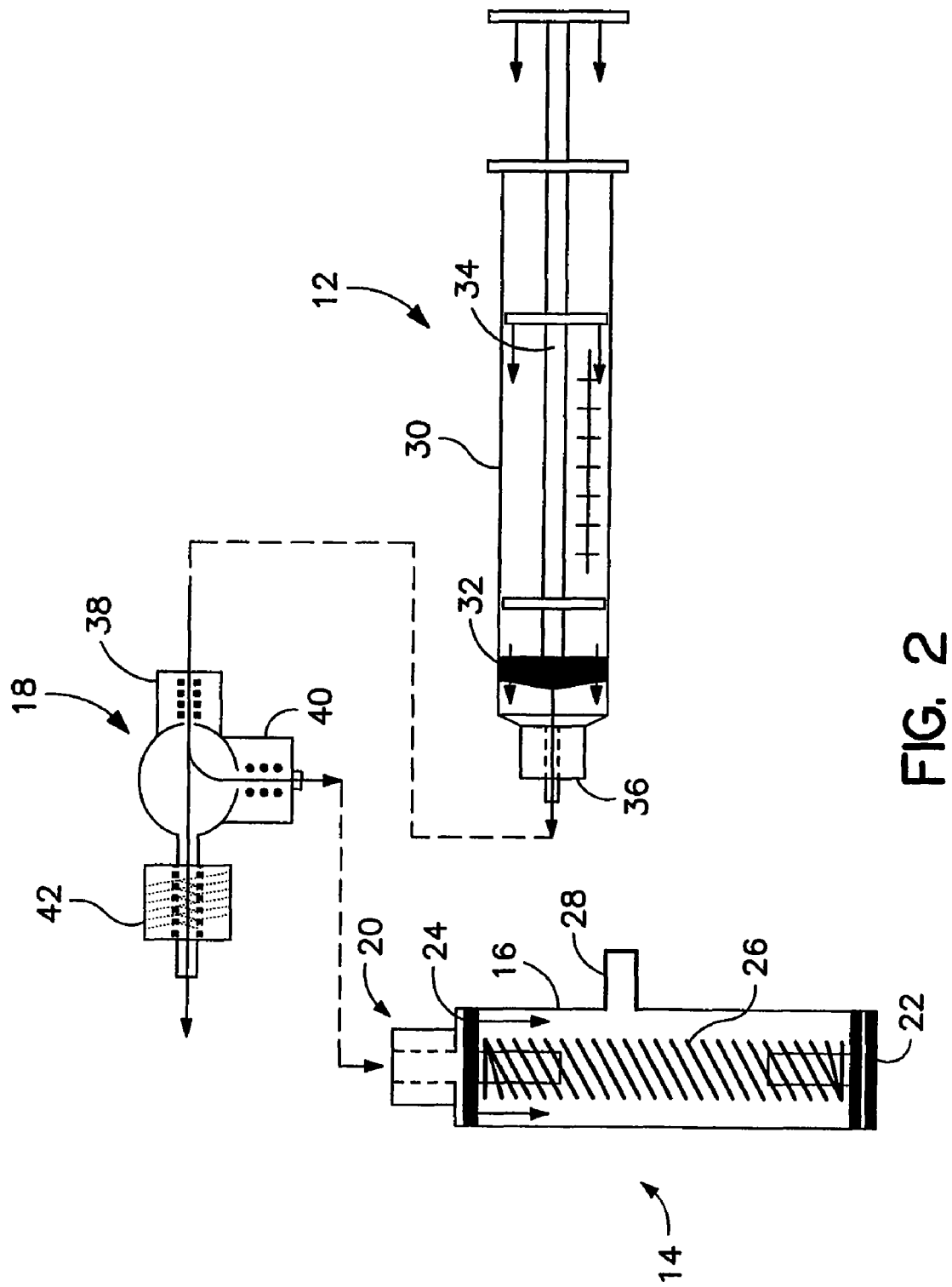
FIG. 2 is an exploded view of the apparatus of FIG. 1.

FIG. 2 shows an exploded view of the apparatus of FIG. 1. This further illustrates the components of the apparatus of this embodiment of the present invention.

As illustrated, syringe 12 is in this embodiment a standard type of syringe, which is well known to a person of ordinary skill in the art. Syringe 12 is adapted for applying a pressure, preferably by injecting a fluid, during a medical procedure. Such a syringe typically includes a tubular portion 30, a plunger 32 slidably disposed within tubular element 30 and a shaft 34 for moving piston 32 within tubular member 30 as desired. An open end 36 of syringe 12 serves as an outlet for fluid being injected using syringe 12, all as is well-known to a person of ordinary skill in the art.

FIG. 2 also further illustrates three-way stop cock 18 which advantageously includes a port 38 for connecting to syringe 12, a port 40 for connecting to pressure regulating member 14, and a port 42 for connecting to a vein to be distended, some intermediate structure to be used in connection with a vein to be distended, or some other apparatus or element to which pressure is to be applied during the relevant medical procedure.

Pressure regulating member 14 has been described further above. In this regard, the positioning of orifice 28 along with selection of spring 26 can be used, along with the typical type of fluid to be injected, to select the appropriate position of orifice 28 along the sidewall of the device. As should be readily apparent, the closer orifice 28 is positioned to open end 20, the smaller the pressure which will be allowed to be applied using apparatus 10 before pressure is released through orifice 28.

Although FIGS. 1 and 2 illustrate a specific embodiment, it should be readily apparent that this device incorporates the general thrust of the present invention which is to provide a pressure regulating member for use in medical procedures which allows for the setting of a maximum pressure beyond which excessive pressure is released. FIGS. 1 and 2 show such a device including the three components described, that is, syringe 12, pressure regulating member 14, and three-way stopcock 18. This is a particularly advantageous configuration of the present invention since syringe 12 and three way stopcock 18 can either be equipment which is readily available or which is at least substantially similar to and thereby comfortable for use by a person of ordinary skill in the art. Of course, apparatus 10 could be provided as a single or integral device, or with the fluid injecting member and pressure regulating member as a single or integral member as well. Many different configurations of such a device fall within the broad scope of the present invention drawn to positioning of a pressure regulating member including a movable plunger or rubber disc for exposure to pressure of the procedure, wherein the plunger or disc is moved by such pressure to expose an orifice which allows release of the pressure.

The components of the device are referred to herein as being made of plastic. Of course, certain materials are desirable depending upon the end use and, it should be readily apparent that various materials can be used to manufacture the apparatus of the present invention with the end-use in mind.

Certain components are also referred to herein as being inelastic. This term includes structures that are substantially inelastic, that is, those having an elasticity which is not significant during use and exposure to the pressures of the relevant medical procedure.

FIG. 3 illustrates an alternative embodiment of pressure regulating member 14 in accordance with the present invention wherein the apparatus is adapted to allow selection of a desired maximum pressure or threshold. As shown, in this embodiment, cylinder 16 has a plurality of openings 44, 46 and 48, and orifice 28 is mounted on a selector member 50 which is positionable relative to openings 44, 46 and 48. In this way, member 50 can be positioned relative to cylinder 16 so as to align orifice 28 with a desired opening 44, 46 or 48, thereby opening and allowing flow therethrough. Member 50 also advantageously covers or block the other non-selected openings. As set forth above, the position of orifice 28 along the sidewall of cylinder 16 sets the maximum pressure. Thus, aligning orifice 28 with opening 44 would provide the lowest maximum pressure and, thereby, the most protection for a conduit or other item to which pressure is to be applied, while opening 48 when aligned with orifice 28 will allow the highest maximum pressure to be applied. Member 50 can advantageously be movably mounted relative to cylinder 16, for example in a track mounted on the outside of cylinder 16. Of course, other configurations can be used to positionably mount orifice 28 relative to a plurality of openings in cylinder 16.

As set forth above, the apparatus of the present invention is also useful when limiting the maximum negative pressure which can be applied.

Figure 6:
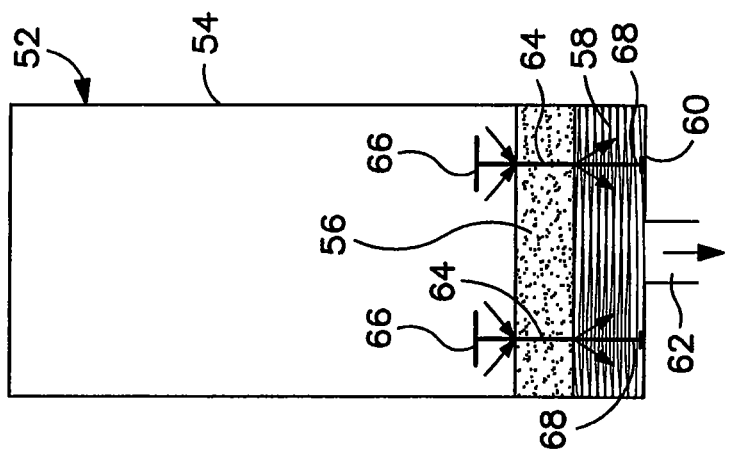
FIGS. 4-6 illustrate an embodiment of the present invention for use in regulating the maximum negative pressure.
Figure 5:
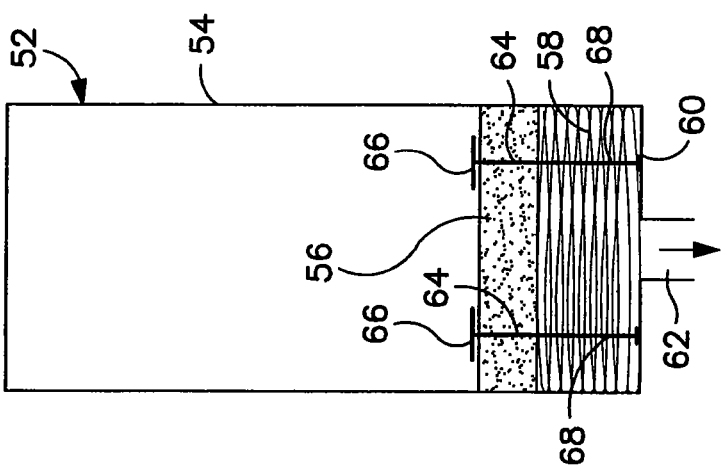
Figure 4:
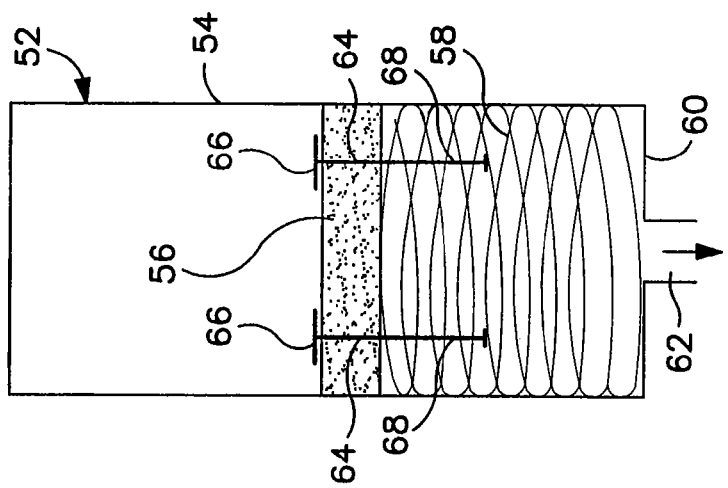

FIGS. 4-6 sequentially illustrate operation of an embodiment of the present invention adapted for use in such negative pressure applications. FIG. 4 illustrates a pressure regulating member 52 which includes a housing 54 in which is mounted a slidable piston 56. A spring or other biasing member 58 is positioned between piston 56 and an end 60 of housing 54 within which an opening 62 is mounted and communicated with a vessel used for applying the desired negative pressure or vacuum. Piston 56 has several openings 64 positioned therein, and release plungers 66 slidably positioned therein. Application of vacuum to piston 56 serves to hold plunger 66 in position within opening 64 as desired, thereby holding the negative pressure. As negative pressure is increased, piston 56 moves toward end wall 60 as shown in FIG. 5. Also as shown, release plungers 66 have an extended body and forwardly projecting tips 68 which eventually reach and contact end wall 60 as shown in FIG. 5. Increase of negative pressure applied to piston 56 once piston 56 has reached this position moves piston 56 towards end wall 60 while release plungers 66 are held in place thereby allowing flow through opening 64 to release vacuum or negative pressure as desired.

In this regard, housing 52 can be open to or at least communicated with a source of substantially ambient pressure, or alternatively the space within housing 52 can be utilized as sufficient additional volume to absorb excess negative pressure being applied. Since the present invention is desired to provide an absolute maximum limit upon application of certain pressures, it is preferred for housing 52 to be communicated with a source of substantially ambient pressure.

In use, pressure regulating member 52 could advantageously be communicated with a device for applying negative pressure, for example through a three-way stopcock 18 as illustrated in the embodiment of FIGS. 1 and 2. In such an embodiment, three-way stopcock would be also communicated with a source of vacuum or negative pressure, which can be in the form of a general supply of such negative pressure which is typically available in medical facilities, or a plunger adapted for pulling a negative pressure or the like.

It should be readily appreciated that the present invention has provided an apparatus which can advantageously be used to limit the maximum pressure or negative pressure applied during medical procedures. The invention has been illustrated in the specific use of limiting pressure applied to conduits such as veins or arteries during a harvesting procedure, which is a particularly advantageous application of the apparatus in accordance with the present invention. Of course, the apparatus finds other useful applications within the broad scope of the present invention as well.

It is to be understood that the invention is not limited to illustrations described and shown herein which are deemed to be merely illustrative of the best modes of carrying out the invention and which are susceptible to modification of form, size, and arrangement of parts and details of operation. The invention rather is intended to encompass all such modifications which are within its spirit and scope as defined by the claims.

What is claimed:

1. An apparatus for regulating pressure applied during a medical procedure, comprising:
    a cylindrical, inelastic housing enclosing an inner volume, the cylindrical housing having a first and second end at first and second ends of a cylinder forming said cylindrical housing, and a plunger for applying pressure to the inner volume, said plunger being slidably disposed within said cylindrical inelastic housing;
    an aperture in the housing for conveying pressure from the housing during the medical procedure; and
    a pressure-operated valve coupled between the inner volume of the housing and a space outside of the inner volume of the housing, in fluid communication with the inner volume of the housing for allowing pressure to escape from the inner volume of the housing through the valve when pressure in the housing exceeds a threshold; and
    a selector member mechanically and movably connected as part of said apparatus;
    whereby fluid pressure in the inner housing actuates the valve to release pressure from within the inner volume of the housing, wherein the pressure-operated valve is provided with discrete threshold setting features, said discrete threshold setting features being manually selectable by a user manually contacting said selector member and moving said selector member to one of a plurality of preset positions corresponding to said discrete threshold setting features, respectively, to perform manual selection of a discrete, pre-set threshold pressure level from a plurality of different discrete pre-set threshold pressure levels; and wherein threshold pressure levels intermediate of two of any of said discrete, pre-set threshold pressure levels cannot be selected.

2. The apparatus of claim 1, wherein the pressure-operated valve comprises:
an opening in the housing;
a plunger disposed within the inner volume of the housing;
a spring disposed within the inner volume of the housing, wherein the spring is positioned between the second end of the housing and the plunger, wherein the plunger in a rest position is between the opening and the aperture, and wherein as fluid is inserted into the inner volume of the housing via the aperture, increased pressure within the inner volume of the housing moves the plunger toward the opening.

3. The apparatus of claim 2, wherein the opening is positioned in a side of the housing providing access to the inner volume of the housing, wherein at normal pressure the opening is closer to the second end than the plunger and wherein as pressure within the inner volume of the housing increases so as to move the plunger past the opening, the pressure within the inner housing is released through the opening.

4. The apparatus of claim 1, wherein said discrete threshold setting features comprise a plurality of openings positioned along the housing, and the selector member movably mounted relative to the plurality of openings and positionable so as to selectively open one and block others of the plurality of openings.

5. The apparatus of claim 1, wherein the pressure-operated valve is adapted to release negative pressure from the housing when the negative pressure exceeds the threshold, and wherein the threshold is a maximum negative pressure.

6. The apparatus of claim 5, wherein the pressure-operated valve comprises a housing having an aperture communicated with the inner volume of the housing, a plunger disposed in the housing and having an opening passing therethrough, and a release-plunger positioned in the opening, the release plunger being adapted to be pushed away from the plunger upon movement of the plunger toward the aperture beyond a threshold position whereby negative pressure is released wherein the plunger reduces the threshold position.

7. An apparatus for regulating pressure applied during a medical procedure, comprising:
a housing enclosing an inner volume for conveying a pressurized fluid, the housing comprising a substantially inelastic housing enclosing the inner volume and a plunger movable within the inelastic housing for applying pressure to the inner volume; and
a pressure-operated valve in fluid communication with the inner volume of the housing and adapted to release pressure from the inner volume when fluid pressure in the inner volume is exerted on the pressure operated valve above a threshold fluid pressure level, wherein the pressure-operated valve is provided with a plurality of openings and a selector member positionable by a user, relative to said plurality of openings, to select the threshold fluid pressure level.

8. The apparatus of claim 7, wherein the threshold is set by a spring exerting a force which must be overcome to exceed the threshold, and further comprising a movable member which can be positioned between at least two different positions corresponding to different forces of the spring which must be overcome to exceed the threshold.

9. The apparatus of claim 1, wherein the threshold is set by a spring exerting a force which must be overcome to exceed the threshold, and further comprising a movable member which can be positioned between at least two different positions corresponding to different forces of the spring which must be overcome to exceed the threshold.

10. The apparatus of claim 1, wherein the movable member only causes pressure to be released once the force is overcome.

11. The apparatus of claim 8, wherein the movable member only causes pressure to be released once the force is overcome.

12. An apparatus for regulating pressure applied during a medical procedure, comprising:
an inelastic housing enclosing an inner volume, the housing having a first and second end wherein the housing comprises a cylindrical inelastic housing enclosing the inner volume and a plunger for applying pressure to the inner volume;
an aperture in the housing for conveying pressure from the housing during the medical procedure; and
a pressure-operated valve coupled between the inner volume of the housing and a space outside of the inner volume of the housing for allowing pressure to escape from the inner volume of the housing through the valve when pressure in the housing exceeds a threshold, whereby the valve releases pressure from within the inner volume of the housing, wherein the pressure-operated valve is adapted to allow selection of the threshold, during use, from a plurality of different thresholds, and wherein a plurality of openings are positioned along the housing, said apparatus further comprising a selector member movably mounted relative to the plurality of openings and positionable so as to selectively open one and block others of the plurality of openings.

13. An apparatus for regulating pressure applied during a medical procedure, comprising:
an inelastic housing enclosing an inner volume, the housing having a first and second end wherein the housing comprises a cylindrical inelastic housing enclosing the inner volume and a plunger for applying pressure to the inner volume;
an aperture in the housing for conveying pressure from the housing during the medical procedure; and
a pressure-operated valve coupled between the inner volume of the housing and a space outside of the inner volume of the housing, in fluid communication with the inner volume of the housing for allowing pressure to escape from the inner volume of the housing through the valve when pressure in the housing exceeds a threshold, whereby fluid pressure in the inner housing actuates the valve to release pressure from within the inner volume of the housing, wherein the pressure-operated valve is provided with discrete threshold setting features, said discrete threshold setting features being selectable by a user to select a discrete, pre-set threshold pressure level from a plurality of different discrete pre-set threshold pressure levels, wherein said discrete threshold setting features comprise a plurality of openings positioned along the housing, and further comprising a selector member movably mounted relative to the plurality of openings and positionable so as to selectively open one and block others of the plurality of openings.

14. An apparatus for regulating pressure applied during a medical procedure, said apparatus comprising:
a cylindrical, inelastic housing enclosing an inner volume, the cylindrical housing having a first and second end at first and second ends of a cylinder forming said cylindrical housing, and a plunger for applying pressure to the inner volume, said plunger being slidably disposed within said cylindrical inelastic housing;

an aperture in the housing for conveying pressure from the housing during the medical procedure; and a pressure-operated valve coupled between the inner volume of the housing and a space outside of the inner volume of the housing, in fluid communication with the inner volume of the housing for allowing pressure to escape from the inner volume of the housing through the valve when pressure in the housing exceeds a threshold, whereby fluid pressure in the inner housing actuates the valve to release pressure from within the inner volume of the housing, wherein the pressure-operated valve is provided with at least one discrete threshold setting feature and a selector member, said at least one discrete threshold setting feature being manually selectable by a user manually contacting said selector member to perform manual selection, by moving said selector member relative to said at least one discrete threshold setting feature of a discrete, pre-set threshold pressure level; and wherein threshold pressure levels other than discrete, pre-set threshold pressure levels cannot be selected.

15. An apparatus for regulating pressure applied during a medical procedure, comprising:

a housing enclosing an inner volume for conveying a pressurized fluid, the housing comprising a substantially inelastic housing enclosing the inner volume and a plunger movable within the inelastic housing for applying pressure to the inner volume; and a pressure-operated valve in fluid communication with the inner volume of the housing and adapted to release pressure from the inner volume when fluid pressure in the inner volume is exerted on the pressure operated valve above a threshold fluid pressure level, wherein the pressure-operated valve is provided with at least one discrete threshold setting feature, and a selector member, each said discrete threshold setting feature being cooperable with said selector member to set a discrete threshold fluid pressure level that is distinct from any other settable discrete threshold fluid pressure level, said selector member being positionable by a user, relative to said at least one discrete threshold setting feature, to set the threshold fluid pressure level, and wherein threshold fluid pressure levels, other than a discrete threshold fluid pressure level set by cooperation between said selector member and said at least one discrete threshold setting feature cannot be selected.

* * * * *